United States Patent
Mitchell et al.

(10) Patent No.: US 8,993,003 B2
(45) Date of Patent: Mar. 31, 2015

(54) EMOLLIENT MIXTURE FOR COSMETIC AND PHARMACEUTICAL FORMULATIONS

(75) Inventors: Catherine Mitchell, Duesseldorf (DE); Rolf Kawa, Monhelm (DE); Ulrich Issberner, Rommerskirchen (DE); Achim Ansmann, Erkrath (DE); Bettina Jackwerth, Langenfeld (DE)

(73) Assignee: Cognis IP Management GmbH, Dusseldorf (DE)

( * ) Notice: Subject to any disclaimer, the term of this patent is extended or adjusted under 35 U.S.C. 154(b) by 2335 days.

(21) Appl. No.: 10/926,629

(22) Filed: Aug. 26, 2004

(65) Prior Publication Data
US 2005/0079986 A1    Apr. 14, 2005

(30) Foreign Application Priority Data
Sep. 3, 2003 (DE) .................. 103 41 025

(51) Int. Cl.
*A01N 59/00* (2006.01)
*A61K 33/00* (2006.01)
*A61K 8/37* (2006.01)
*A61K 8/31* (2006.01)
*A61Q 19/00* (2006.01)

(52) U.S. Cl.
CPC ... *A61K 8/37* (2013.01); *A61K 8/31* (2013.01); *A61Q 19/00* (2013.01)
USPC ........................................... 424/715

(58) Field of Classification Search
None
See application file for complete search history.

(56) References Cited

U.S. PATENT DOCUMENTS

| | | | |
|---|---|---|---|
| 4,436,668 A * | 3/1984 | Harder et al. | 558/260 |
| 5,104,586 A * | 4/1992 | Brand et al. | 514/785 |
| 6,218,353 B1 * | 4/2001 | Romack et al. | 510/406 |
| 6,432,419 B2 | 8/2002 | Kahre et al. | |
| 6,482,418 B1 | 11/2002 | Loehl et al. | |
| 2002/0182164 A1 | 12/2002 | Bossmann et al. | |
| 2004/0234561 A1 | 11/2004 | Ansmann et al. | |

FOREIGN PATENT DOCUMENTS

| | | |
|---|---|---|
| DE | 41 19 890 | 12/1992 |
| DE | 101 33 399 | 1/2003 |
| JP | 11/106326 A1 | 4/1999 |
| JP | 2001328918 A | 11/2001 |
| JP | 2002302427 A | 10/2002 |
| JP | 2003026529 A | 1/2003 |
| WO | WO 97/47281 | 12/1997 |
| WO | WO 97/47282 | 12/1997 |
| WO | 03/011421 A2 | 2/2003 |
| WO | 03/051323 A1 | 6/2003 |

OTHER PUBLICATIONS

Garcia, Josefa, Experimental excess volumes of organic carbonate+ alkane systems. Estimation of the parameters of the Nitta-Chao model for this kind of binary mixture. J. Chem. Soc, Faraday, Trans., 1998, 94(12), 1707-1712.*
Dimethyl Carbonate, MSDS, ChemCAS, http://www.chemcas.com/material/cas/archive/616-38-6.asp, last accessed Mar. 23, 2009, pp. 1-7.*
Dimethyl Carbonate, MSDS, http://msds.chem.ox.ac.uk/DI/diethyl_carbonate.html, last accessed Mar. 23, 2009, pp. 1-2.*
n-Paraffins (complex normal paraffin), n-PARAFFINS, http://chemicalland21.com/petrochemical/n-PARAFFINS.htm Last Accessed Oct. 23, 2009, pp. 1-3.*
Shaikh et al., "Organic Carbonates", vol. 96, 1996, pp. 951-976.
Gassenmeier et al., "Cosmetic Lipids and the Skin Barrier", Marcel Dekker, New York, 2002, pp. 319-352.

* cited by examiner

Primary Examiner — Trevor Love
(74) Attorney, Agent, or Firm — Servilla Whitney LLC

(57) ABSTRACT

The invention relates to a water-free oil-based composition which is liquid at 20° C./normal pressure and which contains
(a) 2 to 90% by weight of at least one linear and/or branched dialkyl carbonate and
(b) 2 to 95% by weight of at least one linear and/or branched alkane containing 8 to 40 carbon atoms
and to its use in the cosmetics field.

10 Claims, No Drawings

EMOLLIENT MIXTURE FOR COSMETIC AND PHARMACEUTICAL FORMULATIONS

BACKGROUND OF THE INVENTION

This invention relates to specific mixtures of oil components which can be incorporated in cosmetic and pharmaceutical preparations, show high dermatological compatibility and provide cosmetic formulations with a particularly light feeling on the skin.

The expert involved in the formulation of cosmetic compositions can choose from a wide range of different emollients, including inter alia silicone oils, esters, ethers, carbonates and alkanes. Each class of compounds has certain sensory characteristics and emollient combinations with high-spreading or low-spreading oils are often used to enable "sensory profiles" to be selectively established on the skin and hair. Oil mixtures with so-called synergistic effects are of particular interest. Silicone oils, particularly readily volatile silicone oils, are frequently used in cosmetic formulations to impart a particularly light feeling on the skin, but unfortunately they have many toxicological and ecological disadvantages.

Accordingly, a search has long been conducted to find substitutes for silicone oils. more particularly emollient mixtures, which would enable cosmetics to be formulated without silicone oils without losing the specific sensory profile of those oils. Substances which are suitable as a complete or partial substitute for silicone oils in order to avoid a buildup effect on the skin and hair are known, for example, from WO 97/47281. The use of oil components selected from the group of dialkyl ethers, dialkyl cyclohexanes, Guerbet alcohols, Guerbet carbonates, ester oils, polyol polyhydroxystearates and/or hydroxycarboxylic acid esters was proposed for this purpose. WO 97/467282 describes cosmetic and/or pharmaceutical preparations containing special dialkyl carbonates and emulsifiers which are distinguished by special sensory properties, the dialkyl carbonates having proved to be equivalent substitutes for silicone oils.

The problem addressed by the present invention was to provide emollient mixtures which would have an improved sensory profile in relation to known compounds and which could be used as substitutes for silicone oils.

It has now surprisingly been found that the sensory profile of oil mixtures often cannot be correlated with that of the individual compounds and that a combination of different oil components or mixtures of oil components has/have a far better sensory profile than the individual compounds.

DESCRIPTION OF THE INVENTION

Accordingly, the present invention relates to water-free oil-based compositions which are liquid at 20° C./normal pressure and which contain (a) 2 to 90% by weight of at least one linear and/or branched dialkyl carbonate and (b) 2 to 95% by weight of at least one linear and/or branched alkane containing 8 to 40 carbon atoms. Preferred compositions according to the invention contain (a) at least 10% by weight of a linear and/or branched dialkyl carbonate and (b) at least 50% by weight of a linear and/or branched alkane containing 8 to 40 carbon atoms. Particularly preferred compositions contain (a) 30 to 70% by weight of dialkyl carbonates and (b) 50 to 90% by weight of $C_{8-40}$ alkane(s) while most particularly preferred compositions contain (a) 30 to 50% by weight dialkyl carbonate(s) and (b) 50 to 90% by weight $C_{8-40}$ alkane(s).

Water-free compositions in the context of the invention are compositions which contain less than 10% by weight water, preferably less than 5% by weight water and more particularly less than 3% by weight water. In a particularly preferred embodiment, the compositions contain only residual quantities of water from the raw materials used.

The compositions according to the invention consist essentially of components (a) and (b) only—apart from impurities and residual quantities of water originating from the raw materials used.

Accordingly, preferred compositions according to the invention are characterized in that the quantities of (a) and (b) add up to 100% by weight, optionally with residual water (c) and optionally impurities (d) emanating from the raw materials used.

The compositions according to the invention typically have a viscosity of 1 to 20 mPa.s at 20° C. (Hoppler viscosimeter; ball 6).

By virtue of their sensory profile, the mixtures according to the invention are particularly suitable as bases in cosmetic and pharmaceutical compositions. They spread easily, are readily absorbed by the skin and leave the skin with a velvety, rather than oily or greasy, feeling. They are therefore also suitable as a substitute for silicone oils.

Dialkyl carbonates and their production are known from the prior art. The dialkyl carbonates may be symmetrical or non-symmetrical, branched or unbranched, saturated or unsaturated. According to the invention, pure substances or mixtures of different dialkyl carbonates may be used. Dialkyl carbonates with $C_{6-24}$ alkyl chains are preferred. Linear or branched, saturated dialkyl carbonates liquid at 20° C./normal pressure are particularly preferred. Di-n-octyl carbonate or di-(2-ethylhexyl)-carbonate or a mixture of these substances is particularly preferred for the purposes of the invention. Of these, di-n-octyl carbonate is preferred.

The compounds may be prepared by transesterification of dimethyl or diethyl carbonate with the corresponding hydroxy compounds using known methods. A review of these methods can be found, for example, in *Chem. Rev.* 96, 951 (1996). Typical examples of dialkyl(ene) carbonates are transesterification products of dimethyl and/or diethyl carbonate with caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachyl alcohol, gadoleyl alcohol, behenyl alcohol, erucyl alcohol and brassidyl alcohol, Guerbet alcohols and the technical mixtures thereof formed, for example, in the high-pressure hydrogenation of technical methyl esters based on fats and oils.

The alkanes usable in accordance with the invention have a chain length of 8 to 40 carbon atoms. They may be branched or unbranched, saturated or unsaturated. $C_{8-40}$ alkanes which are liquid at 20° C./normal pressure are preferred for the purposes of the invention. Of these, branched, saturated $C_{8-40}$ alkanes are preferred. Both pure substances and mixtures may be used. The mixtures are normally mixtures of different isomeric compounds. Compositions containing $C_{10-30}$, preferably $C_{12-20}$ and more particularly $C_{12-20}$ alkanes are particularly preferred. A preferred embodiment of the composition is characterized in that the alkane (b) is a mixture of alkanes containing at least 10% by weight branched alkanes, based on the total quantity of alkanes. The alkanes are preferably branched, saturated alkanes. Another preferred embodiment is characterized in that the alkane (b) is a mixture of alkanes which contains more than 1% by weight 5,8-diethyl dodecane and/or more than 1% by weight didecene.

Cyclic alkanes, such as naphthenic hydrocarbons for example, may also be used in accordance with the invention. However, preferred embodiments of the invention are characterized in that the alkane (b) is a non-cyclic alkane or a mixture of non-cyclic alkanes.

The compositions according to the invention preferably contain no additional oils or waxes other than those mentioned in (a) and (b).

According to the invention, a particularly suitable composition contains (a) 2 to 90% by weight di-n-octyl carbonate and (b) 2 to 95% by weight of a diethyl dodecane or a didecene or an isomer mixtures of these substances. On the basis of the evaluation criteria mentioned in Table 1, mixtures of 30% by weight di-n-octyl carbonate and 70% by weight diethyl dodecane, 10% by weight of di-n-octyl carbonate and 90% by weight diethyl dodecane and a mixture of 50% by weight di-n-octyl carbonate and 50% by weight didecene have the best performance.

The present invention relates to the use of the compositions according to the invention as a silicone oil substitute in cosmetic and pharmaceutical preparations.

Cosmetic/Pharmaceutical Preparations

The compositions according to the invention are used in cosmetic and pharmaceutical preparations in order to give them a very light feeling on the skin. The preparations in question are, for example, body care products formulated as creams, milks, lotions or sprayable emulsions, products for eliminating body odor, etc. The composition according to the invention may also be used in surfactant-containing formulations such as, for example, foam and shower baths, hair shampoos and care rinses. Accordingly, the present invention also relates to cosmetic preparations containing the composition according to the invention as claimed in any of claims 1 to 10. The composition is preferably present in a quantity of 1 to 50% by weight, based on the composition as a whole, and the preparation is preferably free from silicone oils, more particularly cyclomethicone.

The cosmetic preparations may be formulated as emulsions or dispersions which contain water and oil phase alongside one another. Preferred cosmetic compositions are those in the form of a w/o or o/w emulsion with the usual concentrations—familiar to the expert—of oils/fats/waxes, emulsifiers, water and the other auxiliaries and additives typically found in cosmetic preparations.

Depending on their intended application, the cosmetic formulations contain a number of other auxiliaries and additives such as, for example, surface-active substances (surfactants, emulsifiers), other oil components, pearlizing waxes, consistency factors, thickeners, superfatting agents, stabilizers, polymers, fats, waxes, lecithins, phospholipids, biogenic agents, UV protection factors, antioxidants, deodorizers, antiperspirants, anti-dandruff agents, film formers, swelling agents, insect repellents, self-tanning agents, tyrosinase inhibitors (depigmenting agents), hydrotropes, solubilizers, preservatives, perfume oils, dyes and the like which are listed in the following.

The quantities in which the particular additives are used are determined by the intended application.

Surface-Active Substances

The surface-active substances present may be anionic, nonionic, cationic and/or amphoteric or zwitterionic surfactants or emulsifiers or a mixture of these surfactants/emulsifiers. The content of surface-active substances is determined by the type of formulation, but does not normally exceed 20% by weight. Surfactant-containing cosmetic preparations, for example shower gels, foam baths, shampoos, etc., preferably contain at least one anionic surfactant. Body care creams and lotions preferably contain nonionic surfactants/emulsifiers.

Typical examples of anionic surfactants are soaps, alkyl benzene-sulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, polyglycerol esters, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, amino-propionates, aminoglycinates, imidazolinium betaines and sulfobetaines. The surfactants mentioned are all known compounds. Information on their structure and production can be found in relevant synoptic works. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, a-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Body care preparations, such as creams, lotions and milks, normally contain a number of other oil components and emollients which contribute towards further optimization of their sensory properties. The oil components are present in a total quantity of typically 1 to 50% by weight, preferably 5 to 25% by weight and more particularly 5 to 15% by weight. Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols.

Fats and Waxes

Fats and waxes are added as care components to the body care products and also to increase the consistency of the cosmetics. Typical examples of fats are glycerides, i.e. solid or liquid, vegetable or animal products which consist essentially of mixed glycerol esters of higher fatty acids. Fatty acid partial glycerides, i.e. technical mono- and/or diesters of glycerol with $C_{12-18}$ fatty acids, such as for example glycerol mono/dilaurate, palmitate or stearate, are also suitable for this purpose. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Thickeners

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyacrylates (for example Carbopols® and Pemulen types [Goodrich]; Synthalens® [Sigma]; Keltrol types [Kelco]; Sepigel types [Seppic]; Salcare types [Allied Colloids] and Cosmedia® SP and SPL [Cognis]), polyacrylamides, polymers, polyvinyl alcohol, polyvinyl pyrrolidone and bentonites such as, for example, Bentone® GeIVS-5PC (Rheox). Electrolytes, such as sodium chloride and ammonium chloride, are also suitable thickeners.

Stabilizers

Metal salts of fatty acids such as, for example, magnesium, aluminium and/or zinc stearate or ricinoleate may be used as stabilizers.

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene), and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Silicates (talcum), barium sulfate and zinc stearate may be used as salts. The oxides and salts are used in the form of the pigments for skin-care and skin-protecting emulsions.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Deodorizing Components

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers.

Antiperspirant Components

Antiperspirant components reduce perspiration and thus counteract underarm wetness and body odor by influencing the activity of the eccrine sweat glands. Suitable astringent active principles of antiperspirant components are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium Dyes Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

TABLE 1

| | Composition according to the invention | | Absorption | Oiliness | Softness | Velvety feel factor |
|---|---|---|---|---|---|---|
| 1 | 50% di-n-octyl carbonate | 50% diethyl dodecane | 2 | 2 | 1 | 1 |
| 2 | 30% di-n-octyl carbonate | 70% diethyl dodecane | 1 | 1 | 1 | 1 |
| 3 | 10% di-n-octyl carbonate | 90% diethyl dodecane | 1 | 1 | 1 | 1 |
| 4 | 50% di-2-ethylhexyl carbonate | 50% diethyl dodecane | 2 | 2 | 1 | 1 |
| 5 | 50% di-n-octyl carbonate | 50% isohexadecane | 1 | 2 | 1 | 1 |
| 6 | 50% di-n-octyl carbonate | 50% didecene | 1 | 1 | 1 | 1 |
| 7 | 90% di-n-octyl carbonate | 10% diethyl dodecane | 2 | 2 | 2 | 2 |
| C1 | 100% cyclopentasiloxane | | 1 | 1 | 2 | 1 |
| C2 | 100% di-n-octyl carbonate | | 4 | 3 | 4 | 3 |
| C3 | 100% diethyl dodecane | | 3 | 4 | 3 | 3 |
| C4 | 100% didecene | | 3 | 4 | 4 | 4 |
| C5 | 50% di-n-octyl carbonate | 50% di-n-octyl ether | 2 | 3 | 2 | 2 |
| C6 | 50% cocoglyceride | 50% didecene | 4 | 4 | 4 | 4 |
| C7 | 50% di-n-octyl carbonate | 50% cocoglyceride | 5 | 4 | 4 | 4 |
| C8 | 50% dibutyl adipate | 50% di-n-octyl carbonate | 3 | 4 | 5 | 5 |
| C9 | 50% dibutyl adipate | 50% diethyl dodecane | 3 | 4 | 3 | 3 | hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine.

Insect Repellents

Suitable insect repellents are, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the *Kosmetikverordnung* ("Cosmetics Directive").

Perfume Oils and Aromas

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type, are also suitable.

Evaluation in comparison with a cyclomethicone (Dow Corning 245) 1=excellent, 2=very good, 3=good, 4=average, 5=unsatisfactory Mixtures of di-n-octyl carbonate and diethyl dodecane or didecene —the alkane component being an isomer mixture —receive the best sensory evaluation.

Test Group: 10 Experienced and Trained Volunteers.

Quantities of 10 µl of the above-mentioned compositions were applied by micropipette to the hairless side of the forearms of the volunteers and rubbed in with the fingers of the hand of the contralateral side. The sensory profile was evaluated during and after absorption.

The sensory test was carried out on 10 volunteers, as described in the book "*Cosmetic Lipids and the Skin Barrier*" (Marcel Dekker, New York, 2002, Ed. Thomas Förster, pp. 319-352).

The invention claimed is:

1. An emollient mixture consisting essentially of:
    (a) about 2 to about 90% by weight of a carbonate that is selected from the group consisting of di-n-octyl carbonate, di-(2-ethylhexyl)-carbonate, and mixtures thereof; and
    (b) about 2 to about 95% by weight of one or more linear or branched, saturated or unsaturated alkanes having from about 12 to about 20 carbon atoms, all weights being based on the weight of the emollient mixture,
    wherein said emollient mixture is substantially free of water and is liquid at room temperature and pressure, and
    wherein said emollient mixture has superior sensory properties on the skin versus the individual compounds, when incorporated into cosmetic and/or pharmaceutical compositions.

2. The emollient mixture of claim 1 wherein (b) is non-cyclic.

3. The emollient mixture of claim 1 wherein (b) is a mixture of alkanes wherein at least 10% by weight of the alkanes, based on the mixture of alkanes, are branched.

4. The emollient mixture of claim 1 wherein said emollient mixture is free of silicone oils.

5. The emollient mixture of claim 1 wherein the only other components in said emollient mixture are residual water and impurities present in said components (a) and (b).

6. The emollient mixture of claim 1, wherein said sensory properties on the skin are selected from the group consisting of absorption, oily feel, soft feel, velvety feel and combinations thereof.

7. An emollient mixture consisting of:
(a) about 2 to about 90% by weight of a carbonate that consists essentially of di-n-octyl carbonate; and
(b) about 2 to about 95% by weight of an alkane having about 12 carbon atoms, or an alkane mixture having about 12 carbon atoms, all weights being based on the weight of the emollient mixture,
wherein said emollient mixture is substantially free of water and is liquid at room temperature and pressure, and
wherein said emollient mixture has superior sensory properties on the skin versus the individual compounds, when incorporated into cosmetic and/or pharmaceutical compositions.

8. The emollient mixture of claim 1, wherein component (a) consists essentially of di-n-octyl carbonate, and component (b) consists essentially of an alkane having about 12 carbon atoms, or an alkane mixture having about 12 carbon atoms.

9. An emollient mixture consisting essentially of:
(a) about 2 to about 90% by weight of one or more linear and/or branched $C_{6-24}$ dialkyl carbonates; and
(b) about 2 to about 95% by weight of one or more linear or branched, saturated or unsaturated alkanes having from about 12 to about 20 carbon atoms, all weights being based on the weight of the emollient mixture, wherein (b) is a mixture of alkanes wherein at least 1% by weight of the alkanes, based on the mixture of alkanes, is 5,8-diethyldodecane,
wherein said emollient mixture is substantially free of water and is liquid at room temperature and pressure, and
wherein said emollient mixture has superior sensory properties on the skin versus the individual compounds, when incorporated into cosmetic and/or pharmaceutical compositions.

10. An emollient mixture consisting essentially of:
(a) about 2 to about 90% by weight of one or more linear and/or branched C6.24 dialkyl carbonates; and
(b) about 2 to about 95% by weight of one or more linear or branched, saturated or unsaturated alkanes having from about 12 to about 20 carbon atoms, all weights being based on the weight of the emollient mixture, wherein (b) is a mixture of alkanes wherein at least 1% by weight of the alkanes, based on the mixture of alkanes, is didecene,
wherein said emollient mixture is substantially free of water and is liquid at room temperature and pressure, and
wherein said emollient mixture has superior sensory properties on the skin versus the individual compounds, when incorporated into cosmetic and/or pharmaceutical compositions.

* * * * *

UNITED STATES PATENT AND TRADEMARK OFFICE
CERTIFICATE OF CORRECTION

| | | |
|---|---|---|
| PATENT NO. | : 8,993,003 B2 | Page 1 of 1 |
| APPLICATION NO. | : 10/926629 | |
| DATED | : March 31, 2015 | |
| INVENTOR(S) | : Catherine Weichold et al. | |

It is certified that error appears in the above-identified patent and that said Letters Patent is hereby corrected as shown below:

ON THE TITLE PAGE

Item 12 should be changed to read "Weichold, et al."

Item 75 Inventor: "Catherine Mitchell" should be changed to "Catherine Weichold".

Signed and Sealed this
Twenty-seventh Day of October, 2015

Michelle K. Lee
*Director of the United States Patent and Trademark Office*